US012631701B2

(12) United States Patent
Harris et al.

(10) Patent No.: US 12,631,701 B2
(45) Date of Patent: May 19, 2026

(54) SYSTEM AND METHOD FOR INCREASED SAFETY OF AN INTERVENTIONAL RAMPABLE MAGNET

(71) Applicant: Synaptive Medical Inc., Toronto (CA)

(72) Inventors: Chad Tyler Harris, Toronto (CA); Cameron Anthony Piron, Toronto (CA); Alex Gyles Panther, Toronto (CA); Thanh Vinh Vuong, Kitchener (CA)

(73) Assignee: SYNAPTIVE MEDICAL INC.

( * ) Notice: Subject to any disclaimer, the term of this patent is extended or adjusted under 35 U.S.C. 154(b) by 132 days.

(21) Appl. No.: 18/593,553

(22) Filed: Mar. 1, 2024

(65) Prior Publication Data

US 2024/0295618 A1    Sep. 5, 2024

Related U.S. Application Data

(60) Provisional application No. 63/487,656, filed on Mar. 1, 2023.

(51) Int. Cl.
*G01R 33/28* (2006.01)
*G16H 40/20* (2018.01)

(52) U.S. Cl.
CPC ........... *G01R 33/288* (2013.01); *G16H 40/20* (2018.01)

(58) Field of Classification Search
CPC .............................. G01R 33/288; G16H 40/20
See application file for complete search history.

(56) References Cited

U.S. PATENT DOCUMENTS

| | | | | |
|---|---|---|---|---|
| 8,901,928 | B2 * | 12/2014 | Alexiuk | G01R 33/288 |
| | | | | 324/318 |
| 10,079,999 | B2 * | 9/2018 | Van Den Brink ... | G01R 33/288 |
| 10,816,617 | B2 * | 10/2020 | Van Meel | A61B 5/4343 |
| 11,740,307 | B2 | 8/2023 | Sacolick et al. | |
| 12,150,732 | B2 * | 11/2024 | Kawajiri | G07C 9/22 |
| 2014/0002080 | A1 | 1/2014 | Den Harder et al. | |
| 2014/0232400 | A1 | 8/2014 | Kim | |
| 2015/0008918 | A1 | 1/2015 | Nittka | |
| 2015/0362576 | A1 | 12/2015 | Jurrissen et al. | |

(Continued)

FOREIGN PATENT DOCUMENTS

| | | |
|---|---|---|
| WO | WO 2017064539 A1 | 4/2017 |
| WO | WO 2017125790 A1 | 7/2017 |

OTHER PUBLICATIONS

Examiner's Report issued by the Intellectual Property Office of the UK in relation to GB Application No. GB2009676.4 dated Dec. 6, 2020.

(Continued)

*Primary Examiner* — Gregory H Curran

(57) ABSTRACT

A system and method for increased safety of an MRI system is provided. The system includes a rampable main magnet of the MRI system, a main magnet power control for ramping the magnet on and off and a safety device in communication with the main magnet power control, wherein the safety device links the main magnet power control to a safety procedure. The method includes providing a safety device in communication with a power control of a rampable main magnet of the MRI system, wherein the power control ramps the main magnet on and off, and the safety device implements a safety procedure in response to the power control of the magnet.

16 Claims, 9 Drawing Sheets

(56)         References Cited

U.S. PATENT DOCUMENTS

2017/0293005  A1    10/2017  Panther et al.
2018/0052210  A1*    2/2018  Piron ................... G01R 33/288
2023/0349994  A1    11/2023  Sacolick et al.

OTHER PUBLICATIONS

Examiner's Report issued by the Intellectual Property Office of the
UK in relation to GB Application No. GB2009676.4 dated May 9,
2023.

* cited by examiner

SYSTEM AND METHOD FOR INCREASED SAFETY OF AN INTERVENTIONAL RAMPABLE MAGNET

CROSS-REFERENCE TO RELATED APPLICATIONS

This application claims priority from U.S. provisional application No. 63/487,656, filed Mar. 1, 2023, the contents of which are incorporated herein by reference.

TECHNICAL FIELD

The field of the invention is systems and methods for magnetic resonance imaging ("MRI"), in particular safety systems for MRI.

BACKGROUND

MRI systems generally include a main magnet generating a magnetic field tens of thousands of times stronger than the earth's magnetic field. As a result, in certain situations, the main magnet can attract MR-incompatible objects. For example, foreign metal objects, when brought within the vicinity of the magnetic field, can become projectiles flying into the main magnet and causing disastrous damage. In this example, MR-incompatible objects, such as an object including ferromagnetic material, can be attracted by the fringe field of the main magnet.

The MR-incompatible objects may include carts, oxygen tanks, and tools (e.g., metal wrenches). Once attracted, these objects may be accelerated by the magnetic force imparted by the main magnetic field and can become high-velocity projectiles capable of damaging the magnet or harming a human patient or MR operator. This is a significant operational hazard of the MRI system, especially when a patient is being scanned inside the magnet.

Interventional magnetic resonance imaging (iMRI) can provide key information to the surgeon while in or adjacent to the operating room. However, the close proximity of the magnetic field to surgical instruments and devices poses severe safety concerns. Current solutions to mitigate the safety concerns of iMRI require oversight of specially trained MR safety officers and restricted access to certain regions of the operating room.

Certain iMRI systems have the unique capability to turn the main magnetic field off when not in use. This is extremely advantageous from a safety perspective. For example, after surgery, the room must be sanitized. In a typical iMRI suite, extreme care must be taken when sanitizing the room to avoid bringing ferromagnetic objects near the scanner. For iMRI systems in which the main magnetic field can be turned off, the magnetic field can simply be turned off at the end of a procedure, and the room can be sanitized with standard equipment.

Conversely, the ability to turn off the magnetic field could be considered a safety hazard. For instance, one might assume that the system is off when it is actually on. This confusion could have severe consequences.

Thus, there is a need for an improved system and method to regulate and monitor the on/off state of an MRI system so that the safety benefits of a rampable MRI can be fully utilized.

BRIEF DESCRIPTION OF THE DRAWINGS

Embodiments will now be described, by way of example only, with reference to the drawings, in which.

SUMMARY

A system and method for increased safety of an interventional rampable magnet is provided.

Thus by one embodiment, a system includes a rampable main magnet of the MRI system, a main magnet power control for ramping the magnet on and off, and a safety device in communication with the main magnet power control, wherein the safety device links the main magnet power control to a safety procedure.

By a further embodiment, a method includes providing a safety device in communication with a power control of a rampable main magnet of the MRI system, wherein the power control ramps the main magnet on and off, and the safety device implements a safety procedure in response to the power control of the magnet.

DETAILED DESCRIPTION

In order to increase the safety of an MRI or iMRI system, safety devices and safety procedures are linked to the status of the main magnet of the MRI.

Figure 1A:
FIG. 1A shows a perspective view of an example of a magnetic resonance imaging (MRI) system.
Figure 1A:
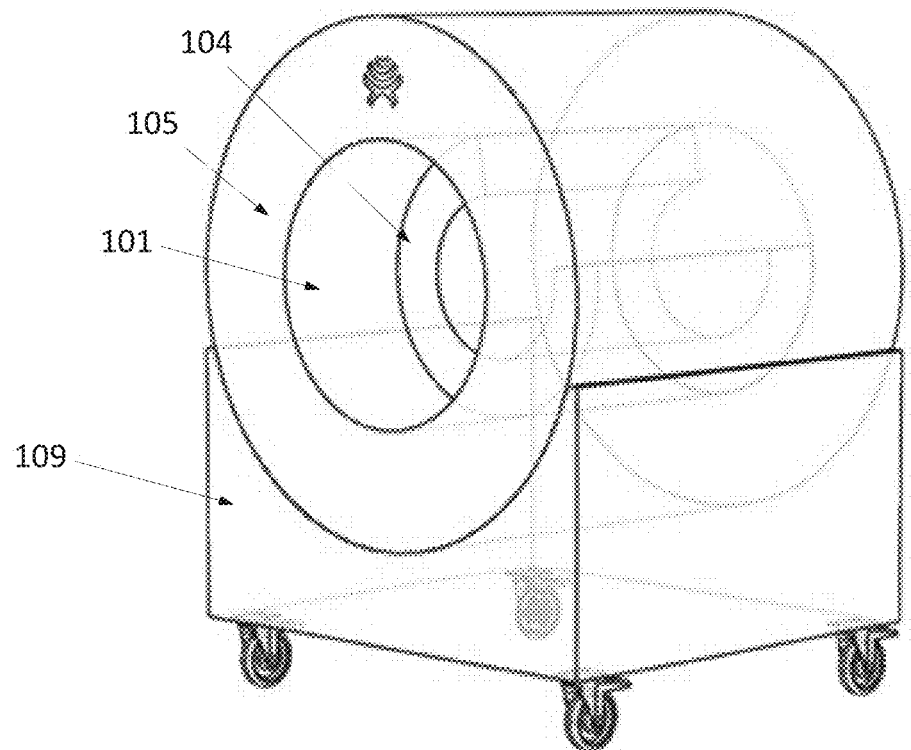

Referring to FIG. 1A, an example of an MRI system 100 is shown in which a magnet housing 105 is placed on a base 109. Base 109 may include a portable cart, as shown. In some installations, base 109 may be affixed to the floor of the scanning room. Magnet housing 105 includes a solenoid magnet and bore area 101, where a human patient may be placed to be scanned. The solenoid magnet may be generally known as the main magnet. The solenoid magnet may generate a substantially uniform magnetic field for imaging the human patient placed inside bore area 101. This magnetic field may generally serve as a static polarizing field.

Figure 1B:
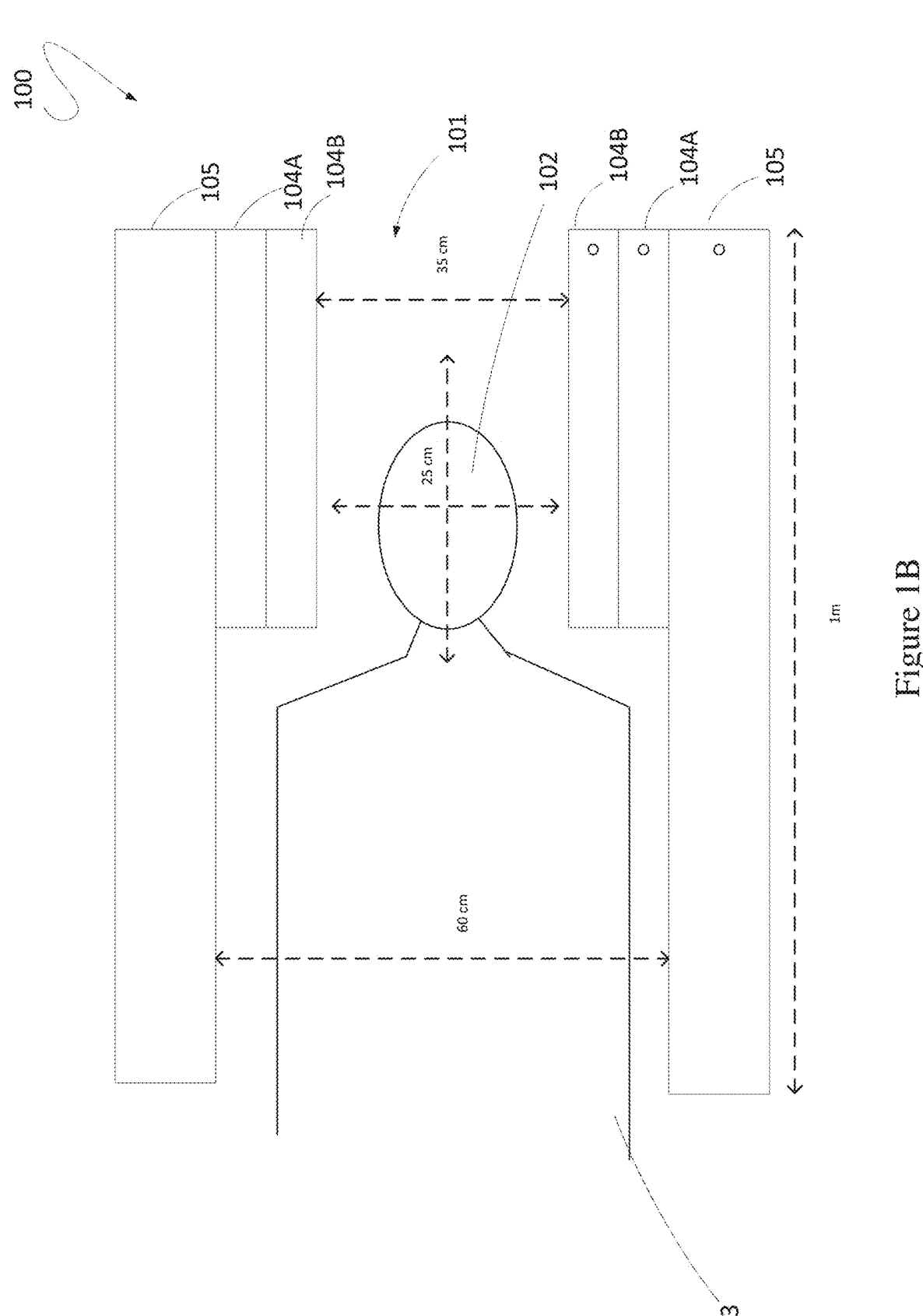
FIG. 1B shows a profile view of the MRI system of FIG. 1A.

Referring to FIG. 1B, patient 103 can be placed in bore area 101. In this example, patient head area 102 is placed inside the magnetic field to be imaged by coil assembly 104. As shown in FIGS. 1A and 1B, coil assembly 104 is shaped as an annular structure and housed within the inner bore of solenoid magnet. In this example, coil assembly 104 includes a gradient coil 104A and a radio frequency (RF) coil 104B. The gradient coil 104A may generate a perturbation of the static polarizing field to encode magnetizations within the human patient's body. In some configurations, coil assembly 104 may include a radio frequency (RF) coil 104B to transmit RF pulses as excitation pulses. The RF coil 104B may also be configured to receive MR signals from the human patient in response to the RF pulses. In another instance, RF coil 104B is used for transmitting an RF signal into the subject and a phased array coil configuration is used for receiving MR signals in response.

Figure 2:
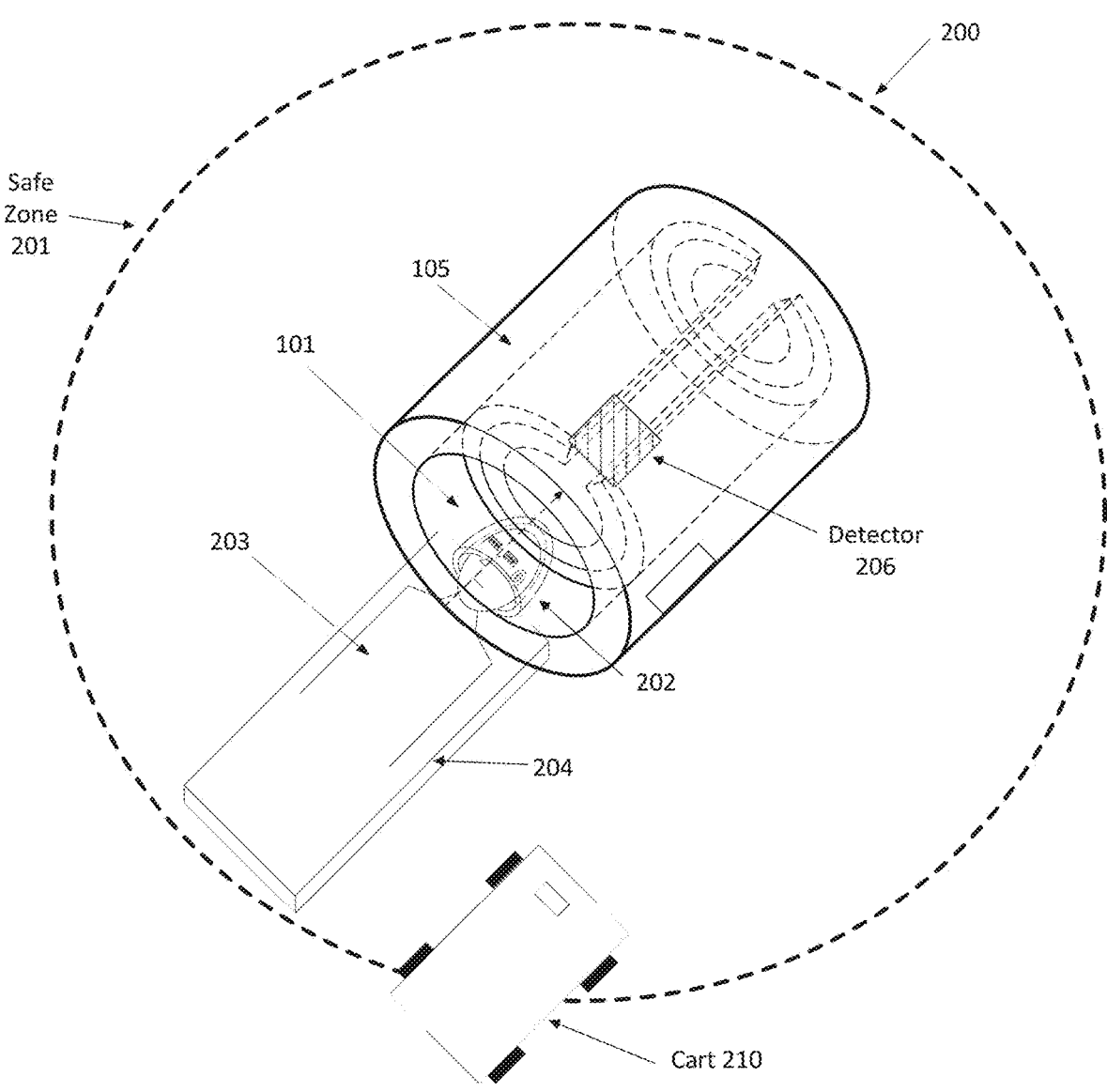
FIG. 2 illustrates an example of an MRI system.

Referring now to FIG. 2, a safety zone 201 may be prescribed inside scanning room 200. In some instances, safety zone 201 extends outside the fringe field (defined by, e.g., the 5 Gauss line) of the magnet. In other instances, safety zone 201 may cover the same area as the fringe field (defined by, e.g., the 5 Gauss line) of the magnet. In still other instances, safety zone 201 may cover an area within the 5-Gauss line perimeter, for example, a 10-Gauss line. Magnet housing 105 includes solenoid magnet and bore area 101, where a human patient 203 may be placed to have an MRI of his or her head region 202. In this illustration, human patient 203 is placed on patient bed 204 that is slideable into bore area 101.

MRI systems commonly contain a superconducting magnet that is kept energized at all times after installation, except perhaps during servicing or emergencies. However, some MRI systems have the capability to turn the main magnet off when not in use. This is extremely advantageous from a safety perspective. For example, at the end of a procedure, the magnetic field can be turned off, and the room can be sanitized with standard equipment. Conversely, the option to turn off the magnetic field may also present a safety hazard, for instance if the status of the magnet is not known or it is assumed that the system is off when it is actually on.

In the present disclosure, "ramp on" or "ramp up" refers to increasing the main magnetic field of the system to its operating level (increasing the current present in the magnet wires). "Ramp off" or "ramp down" means decreasing the main magnetic field of the system to zero (when current is not present in the magnet wires). Ramp status refers to the state of the system (e.g. magnetic field present, no magnetic field present, currently in the process of ramping up or down). A rampable magnet is one that is capable of removing its magnetic field completely and restoring it back to its operating value. Ramping on and off can also be referred to as the magnet being turned on or ramped on, and turned off or ramped off respectively, which results in the magnetic field being turned on and off.

A system for safe operation of an MRI is provided, including a rampable main magnet and a power control for ramping the main magnet on and off. A safety device communicates with the main magnet power control and links the power control to a safety procedure.

In one embodiment, the magnet cannot be ramped on unless a safety officer has signed into a system console, in which case the console functions as a sign-on console, in addition to any other functions. Signing in by the safety office may consist of presenting the console with a password, a radio-frequency identification (RFID) badge, a hospital badge, biometric data such as the results of a facial or fingerprint scan, or other such presentation linking the safety officer to the sign-in procedure. Once the safety officer has signed into the system through the console, the system then allows a user to turn on the magnet (ramp up the magnetic field), in at least one embodiment thereby allowing the power control to ramp the magnet on.

In an extension of this embodiment, the safety officer is prohibited from signing out from the system through the system console unless the magnet has been turned off or a second safety officer has signed in.

FIGS. 3A to 3D are diagrams illustrating top plan views of an interoperative MRI (iMRI) operating room 300 workflow with an MRI system 310. According to FIG. 3A, the power control of the MRI system 310 has ramped down the magnet, and there is no magnetic field. The power control cannot ramp on the magnetic field until a safety officer has logged into the console 320. In some embodiments, the console 320 comprises a dedicated safety console.

Figure 3A:
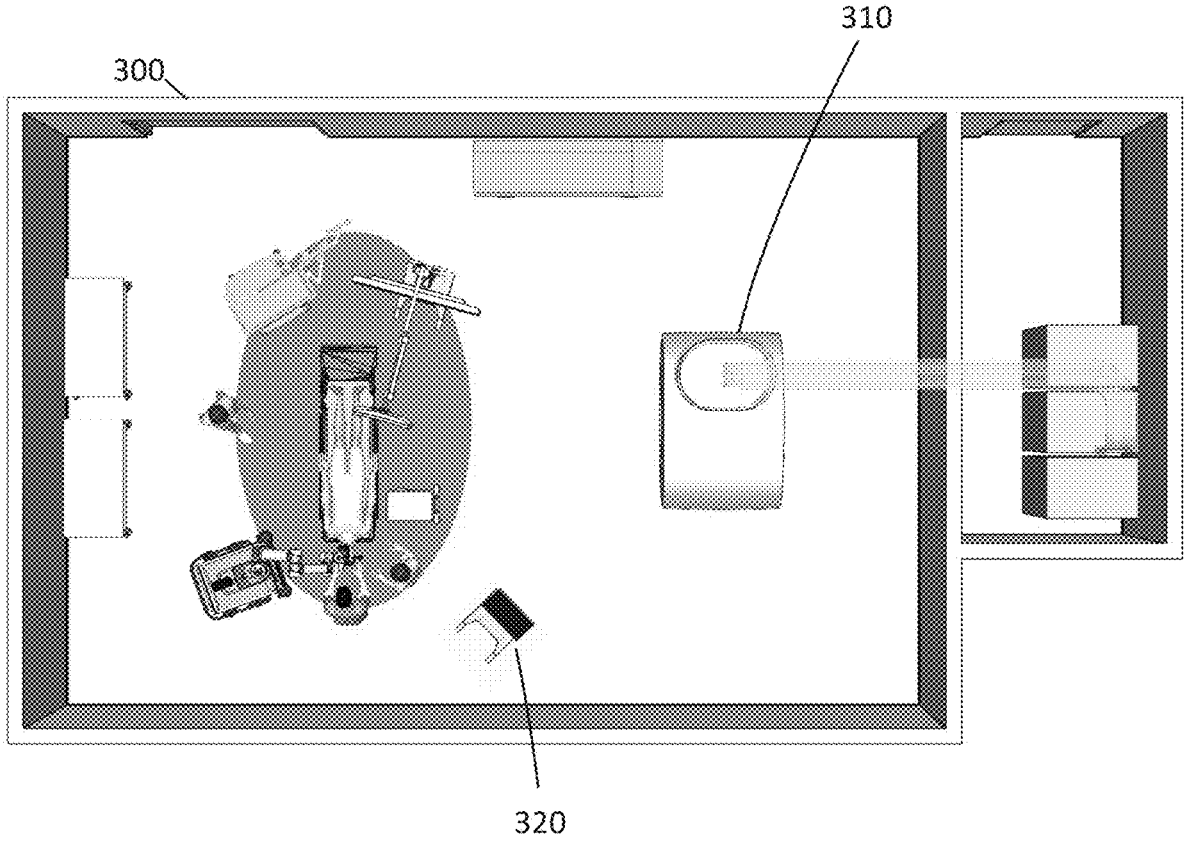
FIG. 3A is a diagram of a top plan view of an interoperative MRI (iMRI) operating room showing step 1 of an exemplary magnet on/off procedure.
Figure 3B:
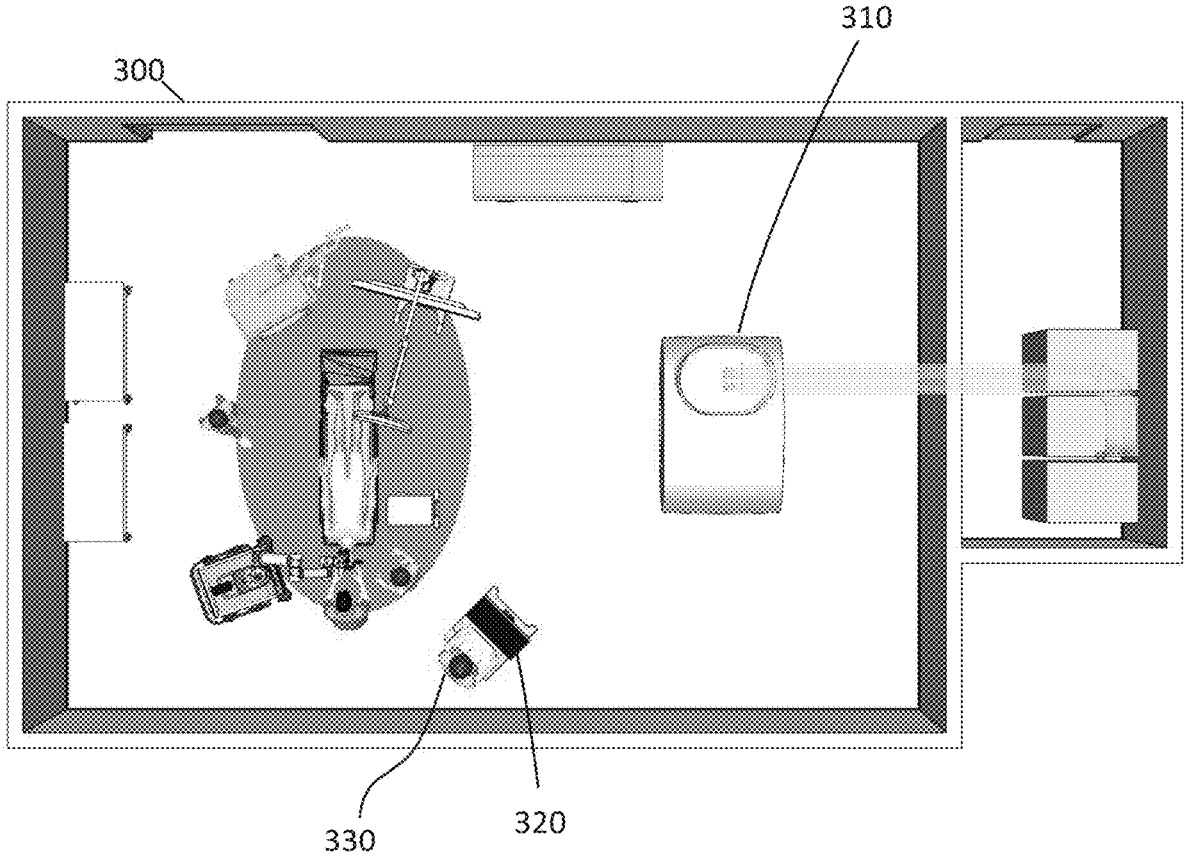
FIG. 3B is a diagram of the top plan view of an iMRI operating room of FIG. 3A, showing step 2 of an exemplary magnet on/off procedure.

According to FIG. 3B, once the safety Officer 330 has logged into the console 320, the power control of the MRI system 310 gains the ability to turn on the magnet and ramp up the magnetic field.

Figure 3C:
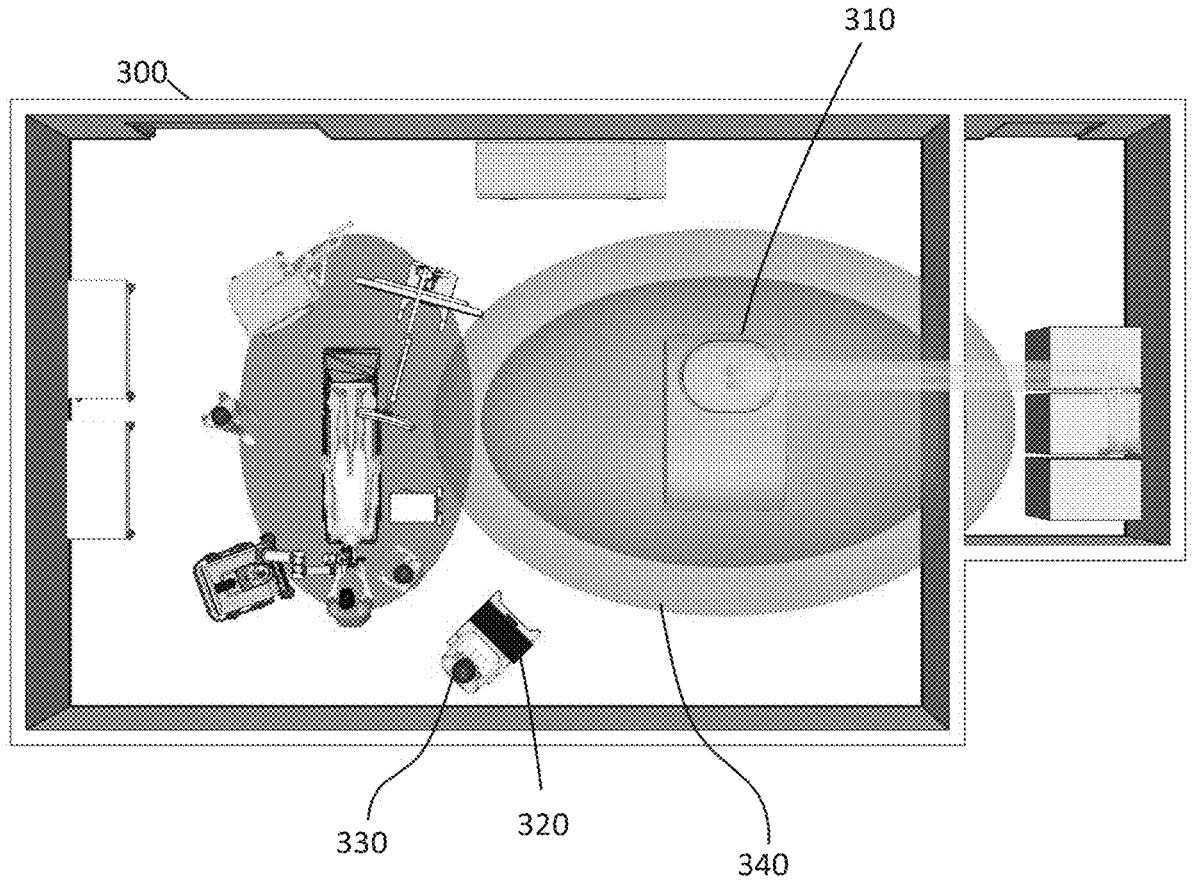
FIG. 3C is a diagram of the top plan view of an iMRI operating room of FIG. 3A, showing step 3 of an exemplary magnet on/off procedure.

According to FIG. 3C, when the power control ramps up the magnetic field (i.e., there is a magnetic field 340 present), the safety officer 330 is unable to log out from the system console until either the power control has ramped down the magnetic field 340 (i.e., turned off the magnet) or a second safety officer has logged in to the system console. This ensures that a safety officer is present while the MRI system is operating and the magnetic field is ramped on.

Figure 3D:
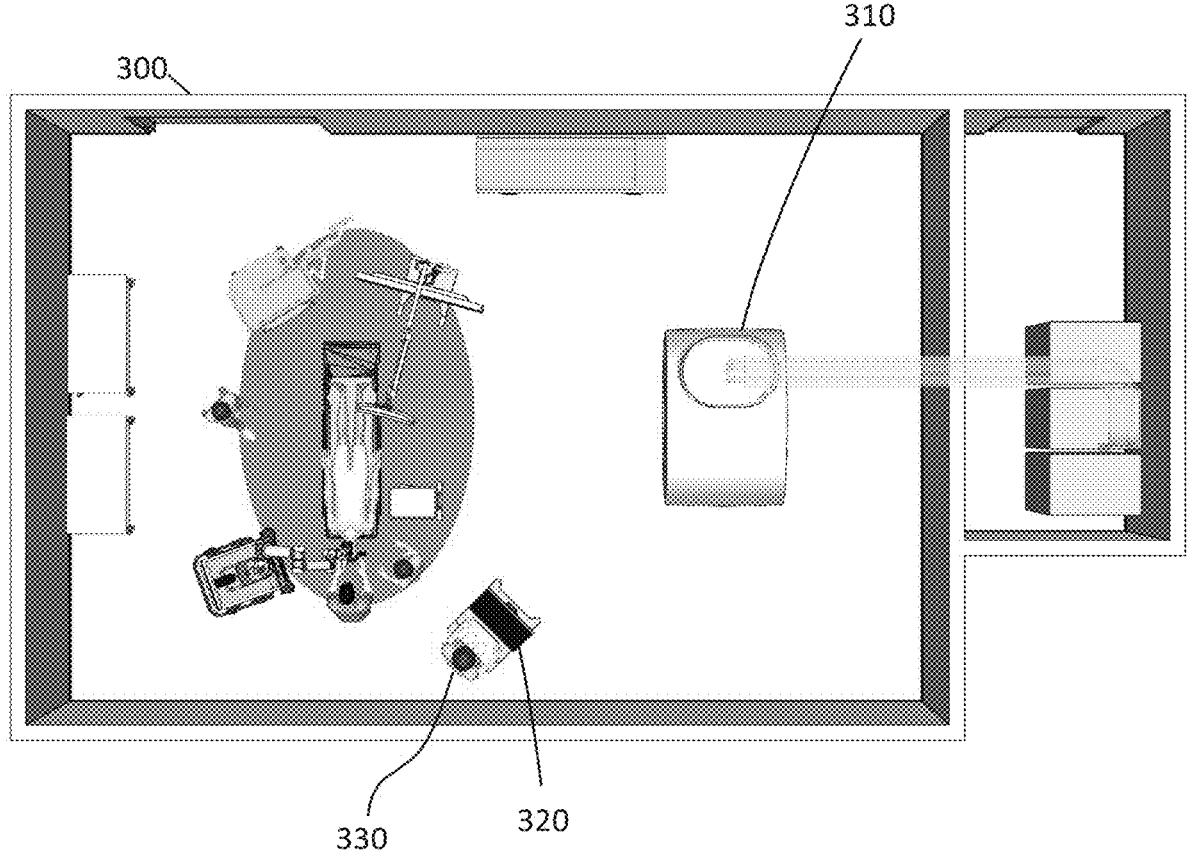
FIG. 3D is a diagram of the top plan view of an iMRI operating room of FIG. 3A, showing step 4 of an exemplary magnet on/off procedure.

According to FIG. 3D, once the magnetic field 340 has been removed by the power control ramping down the magnetic field 340, the safety officer 330 is able to log out of the console 320. Once the safety officer 330 has logged out, the power control cannot ramp up the magnetic field 340 (i.e. turn it back on) until a safety officer 330 has logged into the console again 320.

In another embodiment, the on/off status of the main magnetic field is linked to a door lock. When the magnet is in its off state, and there is no magnetic field, access to the room is freely granted, but when the magnet is turned on, access to the room is restricted to trained personnel. In an extension to this embodiment, access to the room in the magnet off status may be restricted but may not require MR safety training to enter. When the magnet is turned on, safety training is required to access the room, in most implemented environments or embodiments.

Figure 4A:
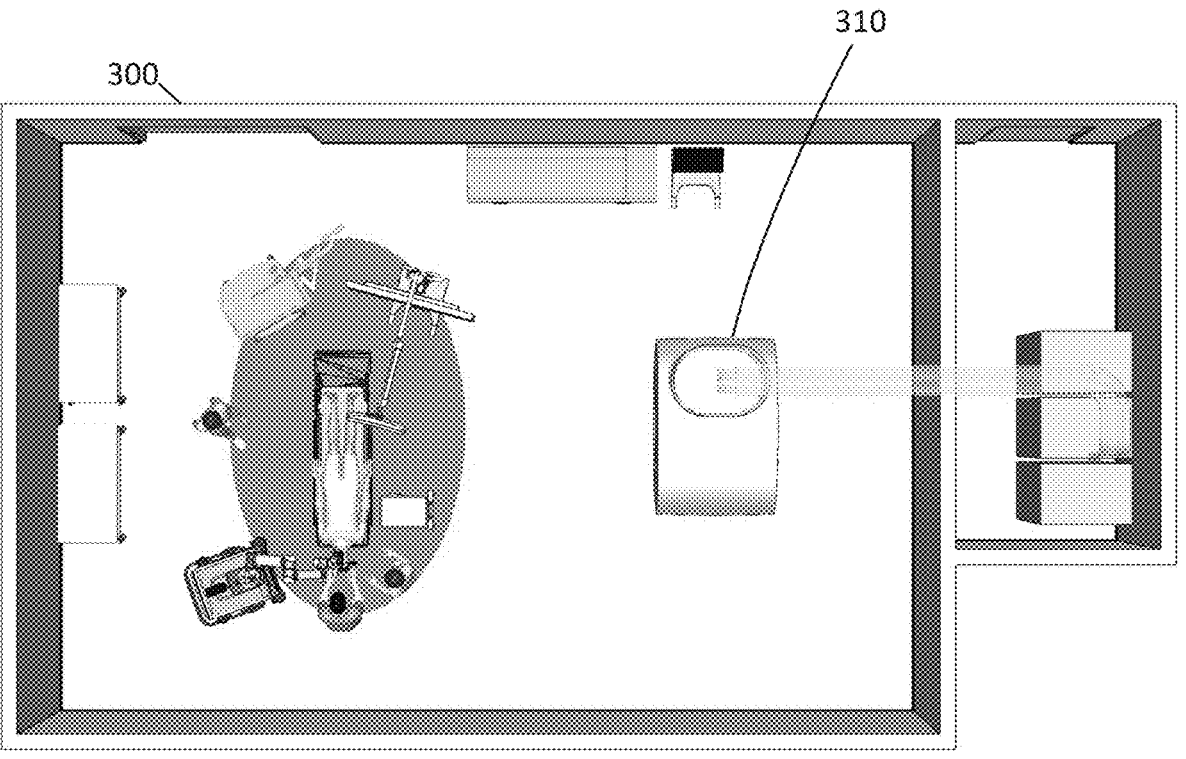
FIG. 4A is a diagram illustrating a top-plan view of an iMRI operating room workflow without a physical barrier deployed when the magnet is in its off state.
Figure 4B:
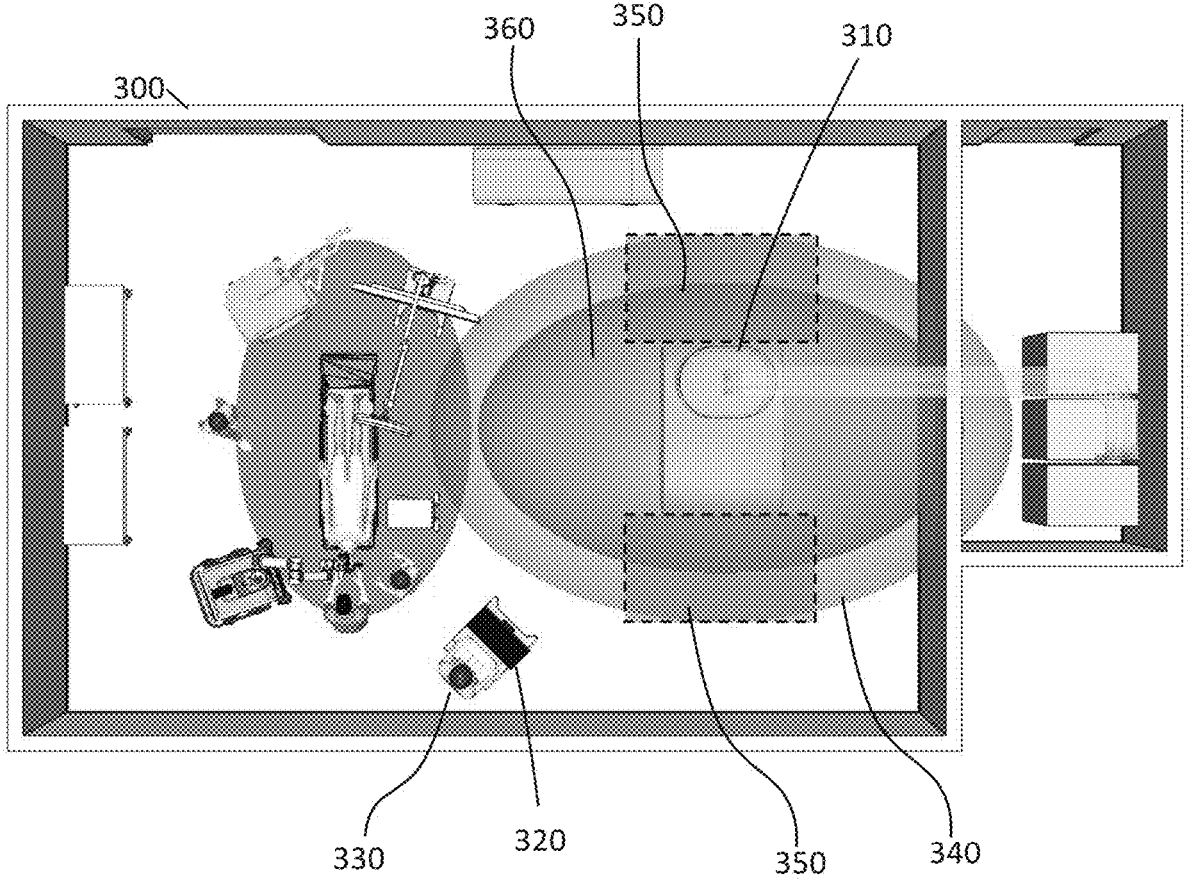
FIG. 4B is a diagram illustrating the top plan view of an iMRI operating room workflow as in FIG. 4A, with a physical barrier deployed when the magnet is in its on state.

In another embodiment, the on/off state of the main magnet is linked to a physical barrier. FIGS. 4A and 4B are diagrams illustrating top plan views of an interoperative MRI (iMRI) 310 operating room 300 workflow with a physical barrier. According to FIG. 4A, when the power control ramps down the magnetic field 340, the barrier (not visible) collapses and allows one to pass nearby to the system 110.

According to FIG. 4B, when the power control ramps up the magnetic field 340, the barrier 350 is extended and restricts movement into a hazard zone 360 of high magnetic field 340. Note that the barrier 350 may only restrict access to a sub-section of the hazard zone 360.

The physical barrier 350 may include a retractable fence and/or an inflatable object that covers all or part of the hazard zone 360 or restricts movement into the hazard zone. Furthermore, the physical barrier 350 may include floodlights, flashing lights, or bright LED lights that shine down at the hazard zone 360. The lights can be bright, flashing, or display certain images to provide an illusion of a hazard zone 360. Furthermore, the physical barrier 350 may also include audible alerts that sound off to indicate that the physical barrier zone is in place (e.g., high-pitch sirens). In at least some embodiments, the barrier includes images produced by lights or projectors.

A further embodiment may include linking the on/off state of the magnetic field to a sign that displays whether the magnetic field is on or off. For example, an electronic sign may display the word "ON" when the magnetic field is on and "OFF" when the magnetic field is off.

A further embodiment may include linking the on/off state of the magnetic field to a passive instrument that signals to hospital personnel that the magnetic field is on or off. For example, the passive instrument may be a ferromagnetic dial that is pulled slightly towards the magnetic field when the system is on and rests away from the system when it is off.

GENERAL CONSIDERATIONS

While some embodiments or aspects of the present disclosure may be implemented in fully functioning computers and computer systems, other embodiments or aspects may be capable of being distributed as a computing product in a variety of forms and may be capable of being applied regardless of the machine or computer-readable media used to affect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as read-only memory (ROM), volatile random access memory (RAM), non-volatile memory, cache or a remote storage device.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor. A "module" can be considered as a processor executing computer-readable code.

A processor as described herein can be a general-purpose processor, a digital signal processor (DSP), an application specific integrated circuit (ASIC), a field programmable gate array (FPGA) or other programmable logic device, discrete gate or transistor logic, discrete hardware components, or any combination thereof configured to perform the functions described herein. A general-purpose processor can be a microprocessor, but in the alternative, the processor can be a controller, or microcontroller, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. In some embodiments, a processor can be a graphics processing unit (GPU). The parallel processing capabilities of GPUs can reduce the amount of time for training and using neural networks (and other machine learning models) compared to central processing units (CPUs). In some embodiments, a processor can be an ASIC including dedicated machine learning circuitry custom-build for one or both of model training and model inference. The disclosed or illustrated tasks can be distributed across multiple processors or computing devices of a computer system, including computing devices that are geographically distributed.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

The specific embodiments described above have been shown by way of example and understood is that these embodiments may be susceptible to various modifications and alternative forms. Further understood is that the claims are not intended to be limited to the forms disclosed, but rather to cover all modifications, equivalents, and alternatives falling within the spirit and scope of this disclosure. While the foregoing written description of the system enables one of ordinary skill to make and use what is considered presently to be the best mode thereof, those of ordinary skill will understand and appreciate the existence of variations, combinations, and equivalents of the specific embodiment, method, and examples herein. The system should therefore not be limited by the above-described embodiment, method, and examples, but by all embodiments and methods within the scope and spirit of the system. Thus, the present disclosure is not intended to be limited to the implementations shown herein but is to be accorded the widest scope consistent with the principles and novel features disclosed herein.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, various changes and modifications in form, material, workpiece, and fabrication material detail may be made, without departing from the spirit and scope of the present disclosure, as set forth in the appended claims, as may be apparent to those of ordinary skill in the art, are also encompassed by the present disclosure.

What is claimed is:

1. A system for safe operation of an MRI system in an MRI room, the system comprising:
   a rampable main magnet of the MRI system;
   a main magnet power control for ramping the magnet on and off; and a safety device in communication with the main magnet power control;

wherein the safety device links the main magnet power control to a safety procedure;

wherein the safety device comprises a sign-on console for a first safety officer and the safety procedure comprises the first safety officer providing a sign-on to the console when the magnet is ramped off, thereby allowing the power control to ramp the magnet on; and the power control is adapted to ramp the magnet down; or a second safety officer must sign on to the safety console;

to allow the first safety officer to log out of the safety console.

2. The system of claim 1, wherein the sign-on comprises at least one of: a password; a radio-frequency identification badge; a hospital badge; and a biometric.

3. The system of claim 1, wherein the safety device comprises a door lock and the safety procedure comprises the door lock restricts access to the room when the power control ramps the magnet on.

4. The system of claim 3, further wherein the door lock restricts access to the room to a trained person when the power control ramps the magnet off and the door lock restricts access to the room to an MR safety trained person when the power control ramps the magnet on.

5. The system of claim 1, wherein the safety device comprises a physical barrier and the safety procedure comprises providing the physical barrier for blocking access to a hazard zone of the MRI room when the power control ramps the magnet on.

6. The system of claim 5, wherein the physical barrier comprises at least one of: a retractable fence; an inflatable object; floodlights; flashing lights; bright LED lights; images produced by lights; and audible alerts.

7. The system of claim 1, wherein the safety device comprises a sign and the safety procedure comprises the sign displaying a ramp status of the magnet.

8. The system of claim 1, wherein the safety device comprises a passive instrument and the safety procedure comprises the instrument signaling a ramp status of the magnet.

9. A method for safe operation of an MRI system in an MRI room, the method comprising:

providing a safety device in communication with a power control of a rampable main magnet of the MRI system, wherein the power control ramps the main magnet on and off; and the safety device implements a safety procedure in response to the power control of the magnet;

wherein the safety device comprises a sign-on console for a first safety officer and the safety procedure comprises the first safety officer providing a sign-on to the console when the power control ramps the magnet off, to allow the power control to ramp the magnet on; and the power control is adapted to ramp the main magnet off; or a second safety officer must provide a sign-on to the console;

to allow the first safety officer to log out of the console.

10. The method of claim 9, wherein the providing a sign-on comprises at least one of: providing a password; providing a radio-frequency identification badge; providing a hospital badge; and providing a biometric.

11. The method of claim 9, wherein the safety device comprises a door lock and the safety procedure comprises the door lock restricts access to the room when the power control ramps off the magnet.

12. The method of claim 11, wherein the door lock restricts access to the room to a trained person when the power control ramps off the magnet and the door lock restricts access to the room to an MR safety trained person when the power control ramps on the magnet.

13. The method of claim 9, wherein the safety device comprises a physical barrier and the safety procedure comprises providing the physical barrier for blocking access to a hazard zone of the MRI room when the power control ramps on the magnet.

14. The method of claim 13, wherein the physical barrier comprises at least one of: a retractable fence; an inflatable object; floodlights; flashing lights; bright LED lights; images produced by lights; and audible alerts.

15. The method of claim 9, wherein the safety device comprises a sign and the safety procedure comprises the sign displaying a ramp status of the magnet.

16. The method of claim 9, wherein the safety device comprises a passive instrument and the safety procedure comprises the instrument signaling a ramp status of the magnet.

* * * * *